United States Patent [19]

Zahler et al.

[11] Patent Number: 4,918,075

[45] Date of Patent: Apr. 17, 1990

[54] PURINYL AND PYRIMIDINYL CYCLOBUTANES AND THEIR USE AS ANTIVIRAL AGENTS

[75] Inventors: Robert Zahler; Glenn A. Jacobs, both of Princeton, N.J.

[73] Assignee: E. R. Squibb & Sons, Inc., Princeton, N.J.

[21] Appl. No.: 286,914

[22] Filed: Dec. 20, 1988

[51] Int. Cl.$^4$ .............. A61K 31/395; A61K 31/495; C07D 473/00; C07F 9/02
[52] U.S. Cl. .................. 514/262; 514/243; 514/258; 514/261; 514/274; 514/81; 544/244; 544/254; 544/265; 544/277; 544/280; 544/313; 544/314; 544/317; 544/264; 544/276; 546/23; 546/118; 549/546
[58] Field of Search .............. 544/254, 265, 277, 280, 544/244, 264, 276; 546/118, 23; 514/243, 258, 261, 262, 303, 81

[56] References Cited

U.S. PATENT DOCUMENTS 4,543,255  9/1985  Shealy et al. ................ 544/256

FOREIGN PATENT DOCUMENTS 159264   10/1985  European Pat. Off. ........... 544/256
0182315   5/1986  European Pat. Off. ........... 544/256
0184473   6/1986  European Pat. Off. ........... 544/256
0219838   4/1987  European Pat. Off. ........... 544/256
03309992  2/1989  European Pat. Off. ........... 514/262

OTHER PUBLICATIONS

Hoshino et al., Inhibition of Infectivity of Human Immunodifficiency Virus by Oxetanocin, J. Antibiotics, 40 (7), 1077 (1987).
Shimada et al., Oxetanocin, A Novel Nucleoside from Bacteria, J. Antibiotics, 39(11), 1623 (1986).
Shealy et al., Synthesis and Antiviral Activity of Carbocyclic Analogues of 2'-Deoxyribofuranosides of 2-Amino-6-substituted-purines and of 2-Amino-6-substituted-8-azapurines, J. Med. Chem., 27, 1416 (1984).
Secrist et al., Resolution of Racemic Carbocyclic Analogues of Purine Nucleosides through the Action of Adenosine Deaminase Antiviral Activity of the Carbocyclic 2'-Deoxyguanosine Enantiomers, J. Med. Chem., 30, 746 (1987).
Canning et al., Synthesis and Antiviral Activity of 9-[-Cis]-2-[Hydroxymethyl)-Cyclopropmethyl]Guanine and Related Compounds, ACS National Meeting, 1986, (Abstract No. 33).
Nakamura, et al., The X-Ray Structure Determination of Oxetanocin, J. Antibiotics, 39, 1626-1629 (1986).
Niitsuma, et al. Studies on the Total Synthesis of Oxetanocin; I. The First Synthesis of a Nucleoside Having Oxetanosyl-N-Glycoside, Tetrahedron Letters, 28, 3967-3970 (1987).
Niitsuma, et al., Studies on the Total Synthesis of Oxetanocin; II. Total Synthesis of Oxetanocin; Tetrahedron Letter, 28, 4713 (1987).
Austin, et al., Chiral Oxetanes from Sugar Lactones: Synthesis of Derivatives of 3,5-Anhydro-1,2-O-Isopropylidene-D-Glucuronic Acid and of 3,5-Anhydro-1,2-O-Isopropylidene-B-L-Iduronic Acid, Tetrahedron Letters, 28, 4741–4744 (1987).
Shimada et al., Derivatives of Oxetanocin: Oxetanocins H, X and G, and 2-Aminooxetanocin A, J. Antibiotics, 40, 1788–1890 (1987).
Y. Nishiyama, et al., Selective Inhibition of Human Cytomegalovirus Replication by a Novel Nucleoside, Oxetanocin G, 32(7), 1053 (1988).
D. Norbeck, et al., Synthesis of (−)-Oxetanocin, J. Am. Chem. Soc., 110, 7217 (1988).
S. Nishiyama, et al., Synthetic Studies on Oxetanocin, A Novel Nucleside with an Oxetane Ring Synthesis of Some Chiral D-Oxetanosyl Acylates, Tetrahedron Letters, 29(37), 4739 (1988).
S. Nishiyama, et al., A Total Synthesis of Oxetanocin, A Novel Nucleoside with an Oxetane Ring, Tetrahedron Letters, 29(37), 4743, (1988).
Derwent Abstract No. 87-296034/42 of Japanese Specification JP-048499 published Sep. 12, 1987.

Primary Examiner—Mary C. Lee
Assistant Examiner—J. Richter
Attorney, Agent, or Firm—Donald J. Barrack; Stephen Venetianer

[57] ABSTRACT

Antiviral activity is exhibited by compounds having the formula

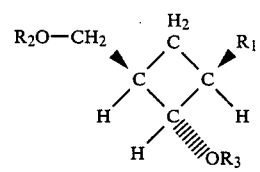

its pharmaceutically acceptable salts thereof wherein $R_2$ and $R_3$ are independently hydrogen, $-PO_3H_2$ or

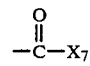

and $R_1$ is either a purine, pyrimidine or an analog thereof.

25 Claims, No Drawings

PURINYL AND PYRIMIDINYL CYCLOBUTANES AND THEIR USE AS ANTIVIRAL AGENTS

BRIEF DESCRIPTION OF THE INVENTION

This application is a continuation-in-part of co-pending application Ser. No. 138,737 filed December 28, 1987, now U.S. Pat. No. 4,855,466.

Antivital activity is exhibited by compounds having the formula

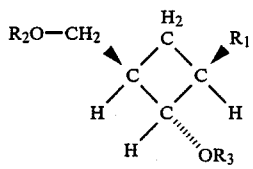

and pharmaceutically acceptable salts thereof. In formula I, and throughout the specification, the symbols are as defined below.

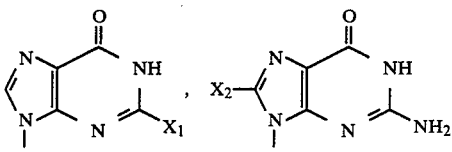

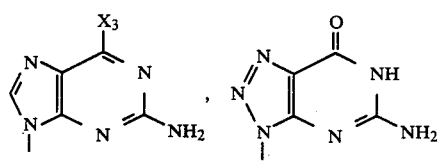

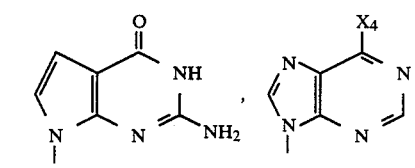

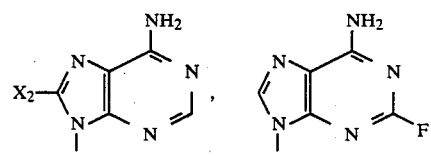

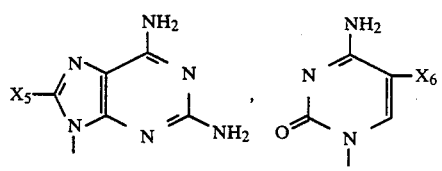

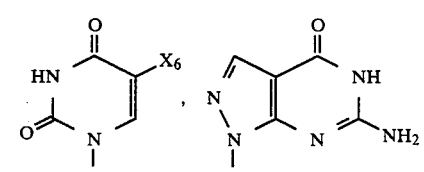

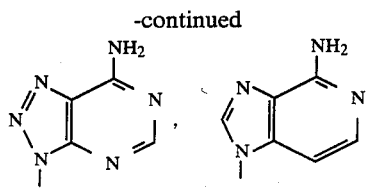

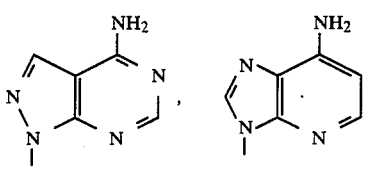

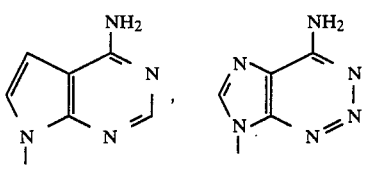

wherein $X_1$ is hydrogen, amino,

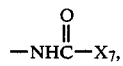

and $-N=CHN(X_8)_2$ $X_2$ is methyl, fluoro, chloro, bromo, iodo, hydroxy, or amino, $X_3$ is hydrogen, chloro, or $O-X_8$, $X_4$ is amino,

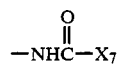

or $-N=CHN(X_8)_2$, $X_5$ is hydrogen, methyl, fluoro, chloro, bromo, iodo, hydroxy, or amino, $X_6$ is fluoro, chloro, bromo, iodo, hydrogen, methyl, trifluoromethyl, ethyl, 2-fluoroethyl, 2-chloroethyl, or

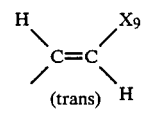

$X_7$ is hydrogen, alkyl, substituted alkyl, or aryl, $X_8$ is alkyl, $X_9$ is chloro, bromo, iodo, hydrogen, or methyl, $R_2$ and $R_3$ are independently hydrogen, $-PO_3H_2$, or

Preferred compounds of formula 1 are wherein $R_1$ is

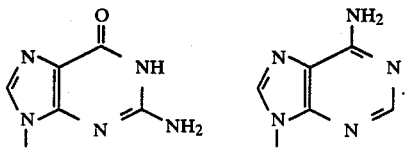

The term "alkyl" refers to both straight and branched chain groups. Those groups having 1 to 10 carbons are preferred. The term "substituted alkyl" refers to alkyl groups having one or more substituents. Preferred substituents are halogen, amino, azido, hydroxy, cyano, trialkylammonium (wherein each alkyl group has 1 to 6 carbons), alkoxy of 1 to 6 carbons, aryl and carboxy. The term "aryl" refers to phenyl and phenyl substituted with one, two or three substituents. Preferred substituents are alkyl of 1 to 6 carbons, alkoxy or 1 to 6 carbons, halogen, trifluoromethyl, amino, alkylamino, dialkylamino, nitro, cyano, alkanoyloxy of 2 to 11 carbons, carboxy, carbamoyl and hydroxy.

DETAILED DESCRIPTION OF THE INVENTION

The compounds of formula 1, and the pharmaceutically acceptable salts thereof, are antiviral agents that can be used to treat viral infection in mammalian species such as domesticated animals (e.g., dogs, cats, horses and the like) and humans, and avian species (e.g., chickens and turkeys). The compounds of formula 1 wherein $R_1$ is

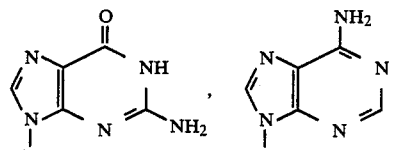

and $R_2$ and $R_3$ are independently hydrogen, $-PO_3H_2$, or

are effective against herpes simplex virus 1 and 2, varicella-zoster virus, cytomegalovirus, vaccinia virus and murine leukemia virus. They may also be effective against other retroviruses and other DNA viruses. Exemplary DNA viruses in addition to those named above include other herpes viruses (e.g., Epstein-Barr virus, pseudorabies virus, and the like), other poxviruses (e.g., monkey pox and myxoma), papovaviruses (e.g., the papilloma viruses), hepatitis B virus, and adenoviruses. Exemplary retroviruses are those effecting man, such as human immunodeficiency viruses (HIV) and human T-cell lymphotropic viruses I and II (HTLV-I and II), and those affecting other animals, such as feline leukemia virus, and equine infectious anemia virus. All of the other compounds in Formula 1 with the exception of wherein $R_1$ is

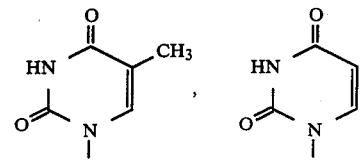

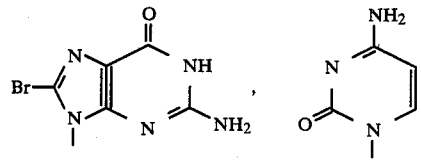

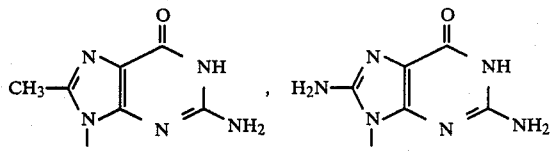

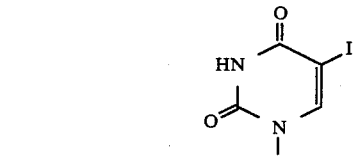

are believed to be active against herpes simplex virus 1 and 2, varicella-zoster virus, cytomegalovirus, and vaccinia virus. They are also believed to be active against the retroviruses and other DNA viruses described above. The compounds of Formula 1 wherein $R_1$ is

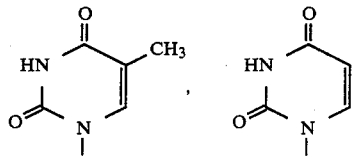

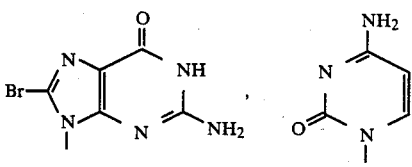

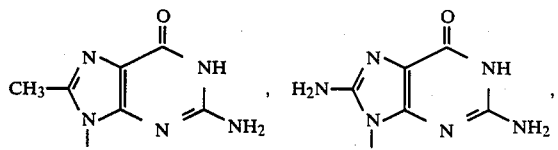

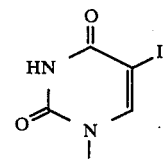

are believed to be active against the various DNA and retroviruses described above with the exception of herpes simplex virus 1 and 2, varicella-zoster virus, cytomegalovirus, and vaccinia virus.

For internal infections, the compounds may be administered orally or parenterally in an amount effective to treat the infection. The dosage will, of course, depend on the severity of the infection, but will likely be in the range of about 1.0 to 30 mg/kg of body weight.

For infections of the eye, or other external tissues, (e.g., mouth and skin) the compositions may be applied to the infected part of the body of the patient topically as an ointment, cream, aerosol, gel, powder, lotion, suspension or solution (e.g., as eye drops). The concentration of the compound in the vehicle will, or course, depend on the severity of the infection, but will likely be in the range of about 0.1 to 7% by weight.

The compounds of this invention can be prepared from the known chemical compound 1-chloro-3-(hydroxymethyl)cyclobutane, which is a racemic mixture of cis and trans diasteriomers. Its hydroxymethyl group is first protected using, for example, a silyl containing group (e.g., a hindered trisubstituted silyl such as t-butyldiphenylsilyl, di-t-butylmethylsilyl, or triisopropylsilyl), trityl, substituted trityl (e.g., 4-monomethoxytrityl or 4,4'-dimethoxytrityl), or benzyl protecting group. The protection reaction yields a compound of the formula

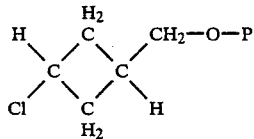

wherein the protecting group "P" serves to protect the hydroxyl group from involvement in subsequent reactions. This protected cyclobutane is a mixture of cis and trans isomers.

Protection with a benzyl group can be accomplished by treating 1-chloro-3-(hydroxymethyl) cyclobutane with sodium hydride in the presence of benzyl bromide in a polar aprotic solvent such as dimethylformamide, dimethylsulfoxide or tetrahydrofuran. Protection with a t-butyldiphenylsilyl group can be accomplished by treating a dimethylformamide solution of 1-chloro-3-(hydroxymethyl)cyclobutane with t-butyldiphenylsilyl chloride in the presence of imidazole. Protection with a trityl or substituted trityl group can be accomplished by (i) treating a pyridine solution of 1-chloro-3-(hydroxymethyl)cyclobutane with trityl chloride or substituted trityl chloride, (ii) treating a dimethylformamide solution of 1-chloro-3-(hydroxymethyl)cyclobutane with trityl chloride or substituted trityl chloride in the presence 4-N,N-dimethylaminopyridine or (iii) treating a dichloromethane solution of 1-chloro-3-(hydroxymethyl)cyclobutane with trityl chloride or substituted trityl chloride in the presence of triethylamine.

Basic elimination of hydrogen chloride from a compound of formula 2 using a base such as potassium t-butoxide in a polar aprotic solvent, such as dimethylsulfoxide or tetrahydrofuran yields the corresponding compound having the formula

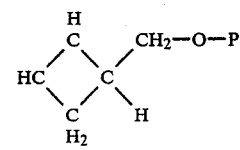

as a racemic mixture. Alternatively, a base such as lithium diisopropylamide in a solvent such as tetrahydrofuran can be used to effect the elimination.

Epoxidation of a compound of formula 3 using a peracid, such as m-chloroperoxybenzoic acid yields the corresponding compound having the formula

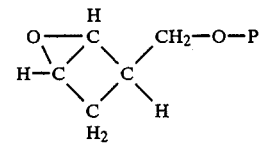

as a racemic mixture of cis and trans diastereomers. Separation of the diastereomers using conventional methodology provides the desired trans stereoisomer having the formula

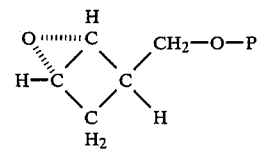

as a racemic mixture. Alternatively, preferential formation of the trans epoxide can be achieved by treating a methanol solution of a compound of formula 3 with benzonitrile/30% hydrogen peroxide in the presence of a buffer (e.g., potassium bicarbonate or monobasic potassium phosphate/sodium hydroxide).

Nucleophilic substitution on the epoxide of a compound of formula 5 using a compound of formula

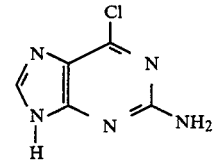

in the presence of a base such as potassium carbonate, sodium hydride, or potassium hydride in an aprotic polar solvent such as dimethylformamide, dimethyl sulfoxide, or sulfolane (tetramethylene sulfone) yields the corresponding compound of formula

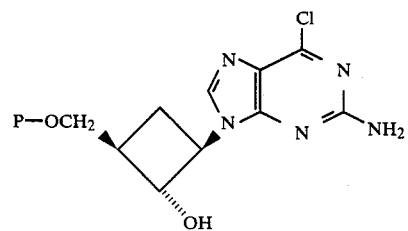

Optionally, the reaction can be run in the presence of a metal chelating catalyst such as 18-crown-6 (1,4,7,10,13,16-hexaoxacyclooctadecane) or 15-crown-5 (1,4,7,10,13-pentaoxacyclopentadecane).

Removal of the protecting group P from a compound of formula 7 yields a compound of formula 1 wherein $R_1$ is

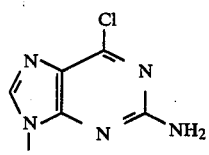

and $R_2$ and $R_3$ are hydrogen. When the protecting group P is benzyl, the group can be removed by treatment with boron trichloride in dichloromethane. When the protecting group P is a silyl protecting group, removal of the group can be accomplished using fluoride ion (e.g., tetrabutylammonium fluoride in tetrahydrofuran). When the protecting group P is a trityl or substituted trityl group, removal of the group can be accomplished using aqueous acid (e.g., aqueous acetic acid) according to methods known in the art.

Reaction of a compound of formula 5 with a protected form of guanine such as a compound of formula

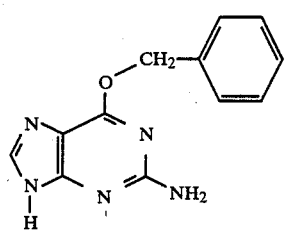

under conditions analogous to those used in the preparation of compound 7 provides a compound of formula

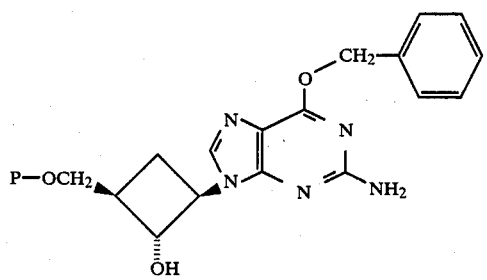

Removal of the protecting groups from a compound of formula 9 yields a compound of formula 1 wherein $R_1$ is

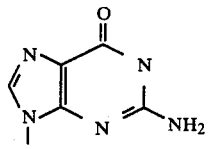

and $R_2$ and $R_3$ are hydrogen.

When the protecting group P in 9 is benzyl, simultaneous removal of the P group and the purine O-benzyl group can be effected by using sodium in liquid ammonia, by hydrogenolysis (e.g., palladium hydroxide on carbon, cyclohexene, and ethanol), or by using boron trichloride in dichloromethane. Alternatively, the purine O-benzyl group can be removed first using aqueous alcoholic mineral acid followed by removal of the P group using, for example, sodium in liquid ammonia or hydrogenolysis. When the protecting group P is a silyl protecting group, removal of the P group can be accomplished using fluoride ion (e.g., tetrabutylammonium fluoride in tetrahydrofuran). The purine O-benzyl group can then be removed with aqueous alcoholic mineral acid, by hydrogeneolysis, or with sodium in liquid ammonia. Alternatively, the purine O-benzyl group can be deprotected first by hydrogenolysis followed by removal of the silyl P group using fluoride ion. When the protecting group P is a trityl or substituted trityl group, removal of the P group and the purine O-benzyl group can be accomplished simultaneously using aqueous/alcoholic mineral acid.

Alternatively this compound of formula 1 can be prepared from a compound of formula 7. For example, when the protecting group P in 7 is benzyl, removal of the P group can be effected first by treatment with boron trichloride, and then the chloro group can be hydrolized using aqueous acid (e.g., aqueous hydrochloric acid). Alternatively, the chloro group can be hydrolized first followed by removal of the benzyl group. When the protecting group P in 7 is silyl, the protecting group can be removed by treatment with fluoride ion, and then the chloro group can be hydrolized. When the protecting group P in 7 is a trityl or substituted trityl group, the protecting group can be removed and the chloro group can be simultaneously hydrolized using aqueous acid.

Alternatively this compound of formula 1 can be prepared by removal of the protecting group P from a compound of formula 7 followed by treatment with adenosine deaminase by methods known in the art (e.g., M. J. Robins and P. W. Hatfield, Can. J. Chem., 60, 547 (1982)).

A compound of formula 1 wherein $R_1$ is

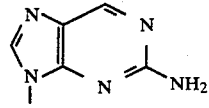

and $R_2$ and $R_3$ are hydrogen can be prepared from a compound of formula 7. For example, when the P group in 7 is benzyl, deprotection and reduction of the chloro group can be accomplished simultaneously by hydrogenation (e.g., ammonium formate and palladium on carbon in methanol; palladium hydroxide on carbon and cyclohexene in ethanol; or palladium on carbon, hydrogen and ethanol). When the P group is silyl the chloro group can first be reduced by hydrogenation and then the protecting group can be removed using fluoride ion. Alternatively, the silyl protecting group can be removed first and then the chloro group can be reduced. When the P group is trityl or substituted trityl, deprotection of the P group can be effected using aqueous acid (e.g., aqueous acetic acid) and the chloro group can then be reduced.

Alternatively, this compound of formula 1 can be prepared by reacting an optionally protected compound of formula 5

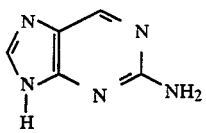
9A with a compound of formula 5 according to the procedures analogous to those used in the preparation of a compound of formula 7, followed by removal of the protecting group(s) by methods known in the art. The optionally protected forms of compound 9A can be protected at the amino (—NH$_2$) group by such exemplary groups as acyl (e.g., acetyl or benzoyl), trityl, or substituted trityl.

A compound of formula 1 wherein R$_1$ is

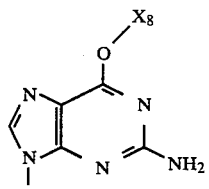

and R$_2$ and R$_3$ are hydrogen can be prepared from a compound of formula 7 or from a compound of formula 1 wherein R$_1$ is

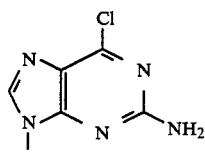

and R$_2$ and R$_3$ are hydrogen by methods known in the art. See, for example, J. F. Gerster, et al., *J. Amer. Chem. Soc.*, 87, 3752 (1965); K. K. Ogilvie, et al., *Can. J. Chem.*, 62, 2702 (1984); M. R. Harnden, et al., *J. Med. Chem.*, 30, 1636 (1987).

Alternatively, this compound of formula 1 can be prepared by reacting a compound of formula

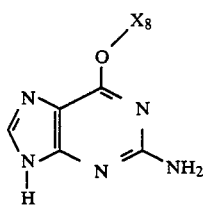
9B with a compound of formula 5 according to the procedures analogous to those used in the preparation of a compound of formula 7, followed by removal of the protecting group P by methods known in the art. Compounds of formula 9B can be prepared from the compound of formula 6 by methods known in the art (see, e.g., W. A. Bowles et. al., *J. Med. Chem.*, 6, 471 (1963)).

A compound of formula 1 wherein R$_1$ is

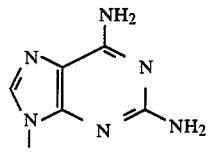

and R$_2$ and R$_3$ are hydrogen can be prepared from a compound of formula 7 by methods known in the art. (See e.g., J. C. Martin, et. al., *J. Med. Chem.*, 28, 358 (1985)). Thus for example, when a compound of formula 7 (wherein P is a protecting group such as benzyl, silyl, trityl or substituted trityl) is treated with hot methanolic ammonia, displacement of the chloro group with an amino group will result. When the protecting group P is a benzyl group, subsequent deprotection can be accomplished by hydrogeneolysis, by sodium in liquid ammonia, or by using boron trichloride. When the protecting group P is a silyl group, subsequent deprotection can be accomplished using fluoride ion. When the protecting group is a trityl or substituted trityl group, subsequent deprotection can be accomplished using an aqueous acid.

Alternatively, this compound of formula 1 can be prepared by reacting an optionally protected compound of formula

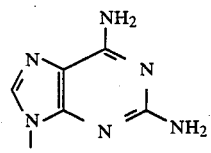
10 with a compound of formula 5 according to the procedures analogous to those used in the preparation of a compound of formula 7, followed by removal of the protecting group(s) by methods known in the art. The optionally protected forms of compound 10 can be protected at the amino (—NH$_2$) groups by such exemplary groups as acyl (e.g. acetyl or benzoyl), trityl, or substituted trityl. When the amino protecting groups are acyl, removal of the acyl groups can be accomplished first using catalytic sodium methoxide in methanol or methanolic ammonia, and then the P protecting group can be removed, for example, by hydrogenolysis when P is benzyl, by treatment with fluoride ion when P is silyl, or by aqueous acid when P is trityl or substituted trityl. Alternatively, the silyl, benzyl or trityl protecting group P could be removed first followed by removal of the acyl protecting groups. When all of the protecting groups are trityl or substituted trityl, simultaneous deprotection of all of the trityl groups can be accomplished using aqueous acid. When the amino protecting groups are trityl and P is benzyl, the trityl groups can be removed first with aqueous acid and the benzyl group can then be removed by hydrogenolysis, sodium in liquid ammonia, or boron trichloride.

Reaction of a compound of formula 5 with an optionally protected compound of formula

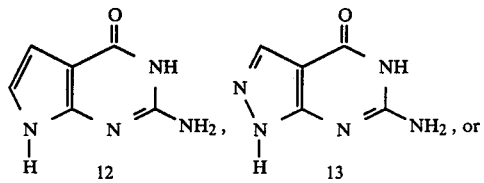

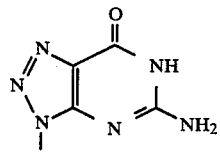

in the presence of a base such as potassium carbonate, sodium hydride, or potassium hydride in a polar aprotic solvent (e.g., dimethylformamide, dimethyl sulfoxide or sulfolane), in the optional presence of 18-crown-6 or 15-crown-5, gives after subsequent removal of the protecting group(s), the corresponding compound of formula 1 wherein $R_1$ is

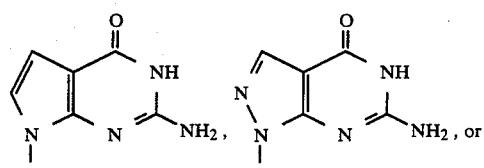

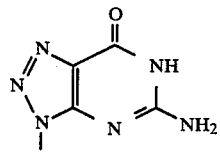

and $R_2$ and $R_3$ are hydrogen.

The optionally protected forms of compounds 12, 13 and 14 can be protected at the amino (—$NH_2$) group by such exemplary groups as acyl (e.g. acetyl or benzoyl), trityl, or substituted trityl. These protecting groups can be removed by methods known in the art.

Alternatively, these compounds of formula 1 can be prepared by reaction of 5 with a compound of the formula

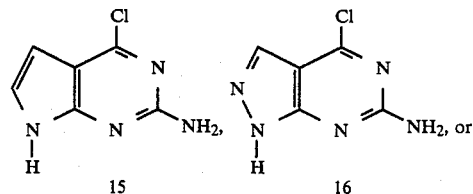

respectively, by procedures analogous to those used in the preparation of 7, followed by acid hydrolysis of the chloro group and simultaneous or subsequent removal of the protecting group P.

Reaction of a compound of formula 5 with a compound of formula

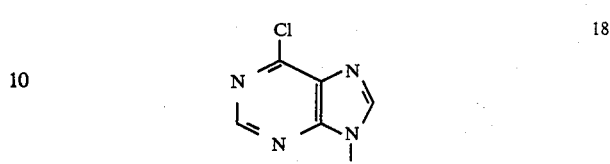

by methodology analogous to that used to prepare a compound of formula 7 yields a compound of formula

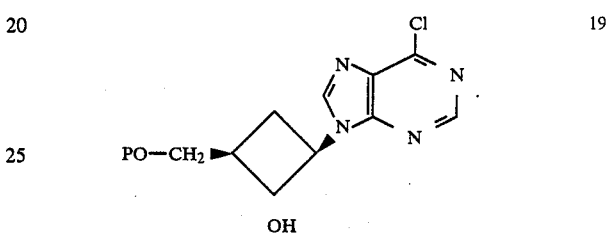

Treatment of a compound of formula 19 with methanolic ammonia and subsequent removal of the protecting group P, yields the compound of formula 1 wherein $R_1$ is

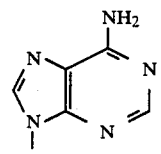

and $R_2$ and $R_3$ are hydrogen.

Alternatively, this compound of formula 1 can be prepared by reaction of a compound of formula 5 with a compound of formula

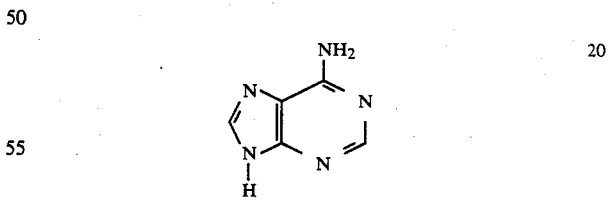

by methodology analogous to that used to prepare a compound of formula 7 and subsequent removal of the protecting group P. If the protecting group P is a benzyl group, this group can be removed by hydrogenolysis (e.g., palladium hydroxide on carbon, cyclohexene, ethanol) or by using sodium in liquid ammonia.

Reaction of the compound of formula 5 with a compound of formula

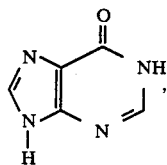

by methodology analogous to that used to prepare a compound of formula 7 and subsequent removal of the protecting group P yields the corresponding compound of formula 1 wherein $R_1$ is

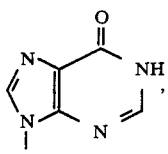

and $R_2$ and $R_3$ are hydrogen.

Alternatively, this compound of formula 1 can be prepared by treatment of the compound of formula 1 wherein $R_1$ is

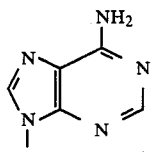

and $R_2$ and $R_3$ are hydrogen with adenosine deaminase or nitrous acid.

Reaction of the compound of formula 5 with a compound of formula

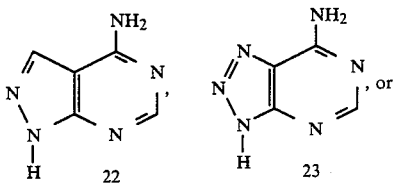

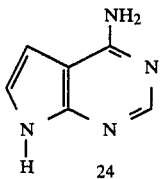

or a protected form thereof, by methodology analogous to that used to prepare a compound of formula 7 and subsequent removal of the protecting groups, yields the corresponding compound of formula 1 wherein $R_1$ is

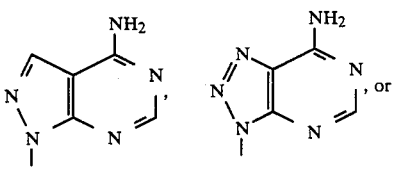

and $R_2$ and $R_3$ are hydrogen.

The protected forms of compounds 22, 23 and 24 can be protected at the amino (—$NH_2$) group by such exemplary groups as acyl (e.g. acetyl or benzoyl), trityl, or substituted trityl. The protecting groups can then be removed by methods known in the art.

Alternatively, these compounds of formula 1 can be prepared by reaction of a compound of formula

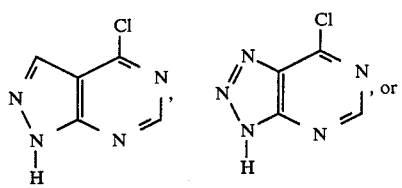

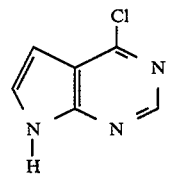

with a compound of formula 5 by methods analogous to those used in the preparation of a compound of formula 7. This affords the corresponding compounds of formula

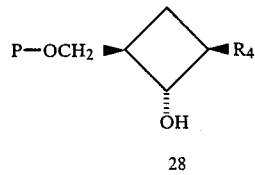

wherein $R_4$ is

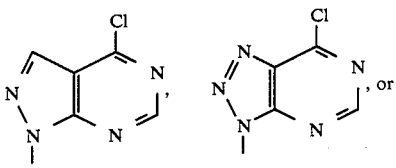

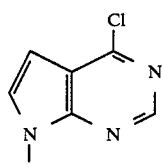

Treatment of a compound of formula 28 with hot ammonia in an alcohol and subsequent deprotection of the P protecting group yields the compound of formula 1 wherein $R_1$ is

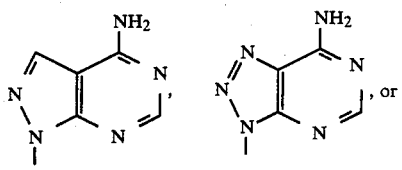

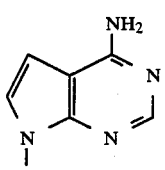

and $R_2$ and $R_3$ are hydrogen.

Reaction of a compound having the formula 5 with an optionally protected compound having the formula

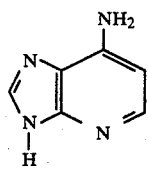

29 following methodology analogous to that used to prepare a compound of formula 7, and subsequent removal of the protecting group(s), yields the corresponding compound of formula 1 wherein $R_1$ is

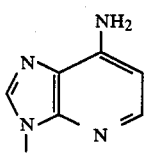

and $R_2$ and $R_3$ are hydrogen. The optionally protected forms of compound 29 are compounds wherein the amino (—$NH_2$) group is protected by such exemplary groups as acyl (e.g. acetyl or benzoyl), trityl or substituted trityl. These groups can then be removed by methods known in the art.

The compound of formula 1 wherein $R_1$ is

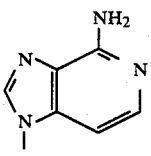

and $R_2$ and $R_3$ are hydrogen can be prepared by reaction of a compound of formula

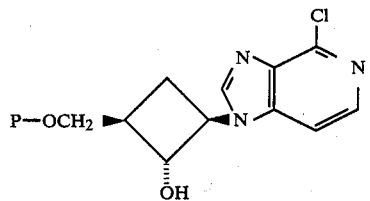

30 with a compound of formula 5, according to the procedures analogous to those used in the preparation of compound 7, which affords an intermediate compound of formula

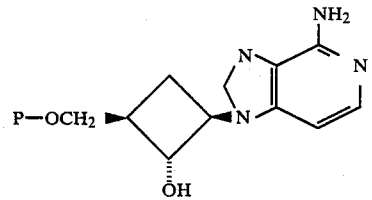

31

Subsequent treatment of the compound of formula 31 with hydrazine, followed by Raney nickel reduction, using methods known in the art (e.g., R. I. Glazer, et al., Biochem. Pharmacol., 35, 4523 (1986); R. J. Rousseau, et al., Biochemistry, 5, 756 (1966)) yields a compound of formula

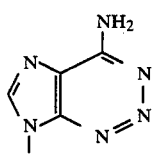

32

The protecting group P in 32 can then be removed by methods known in the art. Alternatively, the protecting group P in 31 can be removed first and the corresponding deprotected compound can then be treated with hydrazine followed by Raney nickel reduction. For example, when P is benzyl, deprotection of 31 can be achieved with boron trichloride. When P is silyl, trityl, or substituted trityl deprotection can be achieved by methods known in the art.

The compound of formula 1 wherein $R_1$ is

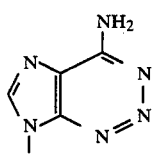

and $R_2$ and $R_3$ are hydrogen can be prepared from a compound of formula 1 wherein $R_1$ is

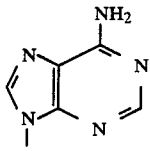

and R₂ and R₃ are hydrogen by methodology known in the art (e.g., the conversion of adenosine to 2-azaadenosine; J. A. Montgomery et al. in "Nucleic Acid Chemistry" Part 2, L. B. Townsend and R. S. Tipson, Eds., John Wiley and Sons, p. 681, 1978).

Compounds of formula

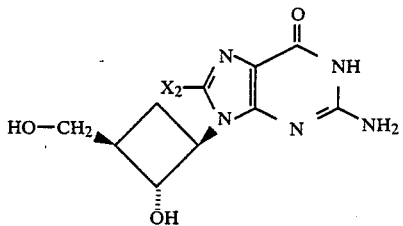

33 wherein $X_2$ is methyl, chloro, bromo, iodo, hydroxy, or amino can be prepared starting from the compound of formula

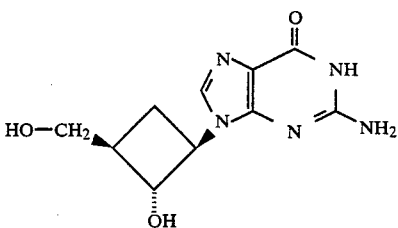

34 by methods known in the art (e.g. M. J. Robins, et al., *J. Med. Chem.*; 27, 1486 (1984)).

For example, treatment of the compound of formula 34 with t-butylhydroperoxide in aqueous sulfuric acid in the presence of ferrous sulfate provides the compound of formula 33 wherein $X_2$ is methyl. Treatment of the compound of formula 34 with dry hydrogen chloride and m-chloroperoxybenzoic acid in dimethylformamide provides the compound of formula 33 wherein $X_2$ is chloro. Treatment of the compound of formula 34 with iodine monochloride in aqueous methanol provides a compound of formula 33 wherein $X_2$ is iodo. Treatment of the compound of formula 34 with bromine water provides the compound of formula 33 wherein X is bromo. Treatment of the compound of formula 33 wherein $X_2$ is bromo with refluxing aqueous hydrazine provides the compound of formula 33 wherein $X_2$ is amino. Treatment of the compound of formula 33 wherein $X_2$ is bromo with sodium acetate/acetic acid provides the compound of formula 33 wherein $X_2$ is hydroxyl.

A compound of formula 33 wherein $X_2$ is fluoro can be prepared from the compound of formula 33 wherein $X_2$ is bromo or iodo and where the amino (—NH₂) and/or hydroxyl groups are optionally protected with acyl (e.g. acetyl or benzoyl) groups. Treatment with fluoride ion (e.g., sodium or potassium fluoride in a solvent such as dimethylformamide or tetrabutylammonium fluoride in tetrahydrofuran) followed by removal of the optional acyl protecting groups using, for example, catalytic sodium methoxide in methanol or methanolic ammonia provides the compound of formula 33 wherein $X_2$ is fluoro.

Compounds of formula 1 wherein $R_1$ is

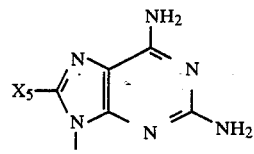

and $X_5$ is methyl, chloro, bromo, iodo, hydroxy, or amino and R₂ and R₃ are hydrogen can be prepared from the corresponding compound of formula 1 wherein $X_5$, R₂ and R₃ are hydrogen using procedures known in the art. See, for example, R. E. Holmes, et al., *J. Amer. Soc.*, 86, 1242 (1964); R. E. Holmes, et al., *J. Amer. Chem. Soc.*, 87, 1772 (1965); R. A. Long, et al., *J. Med. Chem.*, 27, 1486 (1984). The amino (—NH₂) and/or hydroxyl groups in the compound of formula 1, wherein $X_5$, R₂ and R₃ are hydrogen, can be optionally protected by acyl (e.g. acetyl or benzoyl) groups prior to replacement of the $X_5$ hydrogen by a methyl group. Subsequent deprotection can be accomplished by treatment with sodium methoxide in methanol or methanolic ammonia.

The compound of formula 1 wherein R₁ is

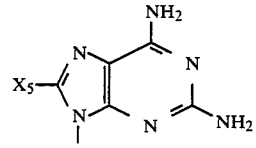

and $X_5$ is fluoro and R₂ and R₃ are hydrogen can be prepared from the corresponding compound of formula 1 wherein $X_5$ is bromo or iodo and R₂ and R₃ are hydrogen. The amino (—NH₂) and/or hydroxyl groups can be optionally protected with acyl (e.g. acetyl or benzoyl) groups. Treatment with fluoride ion (e.g., sodium or potassium fluoride in a solvent such as dimethylformamide or tetrabutylammonium fluoride in tetrahydrofuran) followed by removal of the optional acyl protecting groups (using, for example, catalytic sodium methoxide in methanol or methanolic ammonia) provides the compound of formula 1 wherein R₁ is

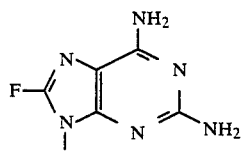

and R₂ and R₃ are hydrogen.

Compounds of formula 1 wherein R₁ is

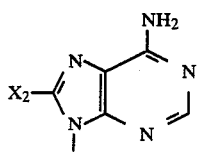

and X₂ is methyl, chloro, bromo, iodo, hydroxy, or amino and R₂ and R₃ are hydrogen can be prepared from the corresponding compound of formula 1 wherein R₁ is

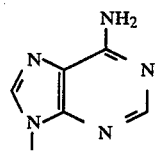

and R₂ and R₃ are hydrogen following procedures known in the art. See, for example, R. E. Holmes, et. al., *J. Amer. Chem. Soc.,* 86, 1242 (1964); R. E. Holmes, et. al., *J. Amer. Chem. Soc.,* 87, 1772 (1965); R. A. Long et. al., *J. Org. Chem.,* 32, 2751 (1967).

A compound of formula 1 wherein R₁ is

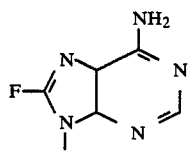

and R₂ and R₃ are hydrogen can be prepared from a compound of formula

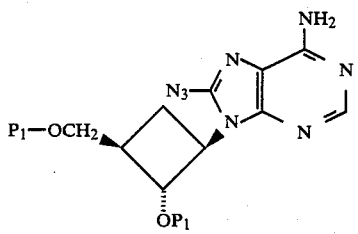

wherein P₁ is an acyl protecting group, (for example, acetyl or benzoyl) by methodology known in the art (e.g., M. Ikehara, et al., *Chem. Commun.,* 1509 (1968)). The compound of formula 35 can be prepared by known methods from the compound of formula 1 wherein R₁ is

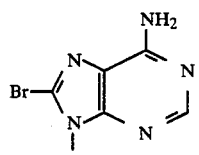

and R₂ and R₃ are hydrogen by treatment with sodium azide followed by acylation of the hydroxyl groups. See, for example, R. A. Long, et al., *J. Org. Chem.,* 32, 2751 (1967).

The compound of formula 1 wherein R₁ is

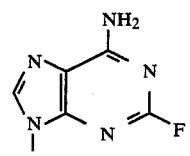

and R₂ and R₃ are hydrogen can be prepared from the corresponding compound of formula 1 wherein R₁ is

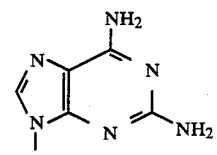

and R₂ and R₃ are hydrogen by following known procedures. See, for example, J. A. Montgomery, et al. in "Synthetic Procedures in Nucleic Acid Chemistry", Vol. 1, W. W. Zorbach and R. S. Tipson, Eds., Interscience Publishers (John Wiley and Sons), N.Y., p. 205, 1968.

The compound of formula

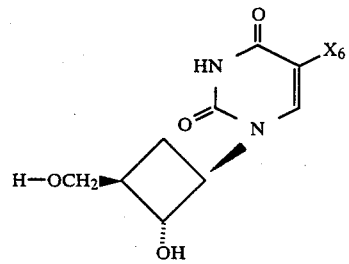

wherein X₆ is hydrogen, fluoro, methyl, ethyl, 2-chloroethyl, or 2-fluoroethyl can be prepared by reaction of the corresponding compound of formula

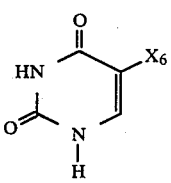

with a compound of formula 5 in the presence of a base such as potassium carbonate, sodium hydride, or potassium hydride, in an aprotic polar solvent (e.g., dimethylformamide, dimethylsulfoxide, or sulfolane), in the optional presence of 18-crown-6 or 15-crown-5, which yields an intermediate of formula

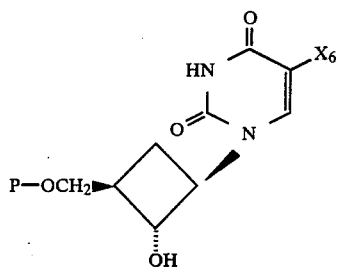

38

Removal of the protecting group P provides the corresponding compound of formula 1 wherein $R_1$ is

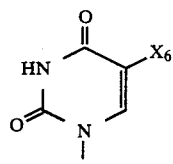

and $R_2$ and $R_3$ are hydrogen.

For example, when P is benzyl, this protecting group can be removed by hydrogenolysis (e.g. palladium hydroxide on carbon and cyclohexene in ethanol) or by treatment with boron trichloride. When P is silyl, deprotection can be accomplished with fluoride ion. When P is trityl or substituted trityl, deprotection can be accomplished with aqueous acid.

The compound of formula 37 wherein $X_6$ is 2-chloroethyl or 2-fluoroethyl can be prepared by methods known in the art [H. Griengl, et al., *J. Med. Chem.*, 30, 1199 (1987); *J. Med. Chem.*, 28, 1679 (1985)].

The compound of formula 36 wherein $X_6$ is fluoro can also be prepared from the corresponding compound 36 wherein $X_6$ is hydrogen and the hydroxy groups are optionally protected with a group such as acyl (e.g. acetyl or benzoyl) by fluorination with trifluoromethyl hypofluorite using methodology known in the art. For example, see M. J. Robins, et al., *J. Amer. Chem. Soc.*, 93, 5277 (1971) and *Chem. Commun.*, 18, 1972; T. S. Lin, et al., *J. Med. Chem.*, 26, 1691 (1983).

Alternatively, compounds of formula 36 wherein $X_6$ is 2-chloroethyl or 2-fluoroethyl can be prepared from a compound of formula

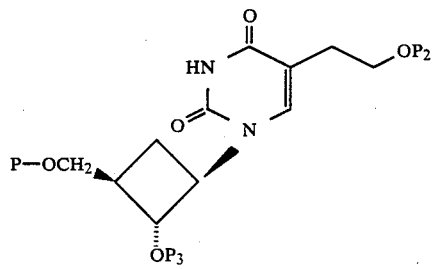

39 wherein P, $P_2$, and $P_3$ are protecting groups wherein $P_2$ can be selectively removed in the presence of P and $P_3$. Protecting groups P and $P_3$ may be the same of different. For example, when $P_2$ is a silyl, trityl, or substituted trityl group, P can be a benzyl group and $P_3$ can be an acyl (e.g., acetyl or benzoyl) group. Selective removal of the protecting group $P_2$ yields a compound having the formula

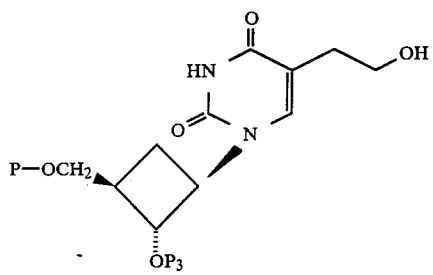

39a

Treatment of compound of formula 39a with triphenylphospine-carbon tetrachloride or diethylaminosulfur trifluoride, and subsequent removal of protecting groups P and $P_3$, affords the compound having the formula 36 wherein $X_6$ is 2-chloroethyl or 2-fluoroethyl, respectively.

Treatment of a compound 39a with triphenylphosphine/N-bromosuccinomide or triphenylphosphine/N-bromosuccinimide/tetrabutylammonium iodide (see H. Griengl, et al., *J. Med. Chem.*, 28, 1679 (1985)) affords compounds having the formula

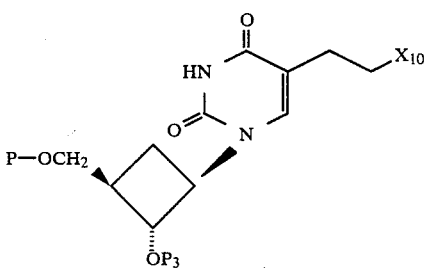

39b wherein $X_{10}$ is bromo and iodo, respectively. Subsequent treatment with fluoride ion, followed by removal of protecting groups P and $P_3$, provides the compound of formula 36 wherein $X_6$ is 2-fluoroethyl.

The compound of formula 39 can be prepared by reaction of a compound having the formula

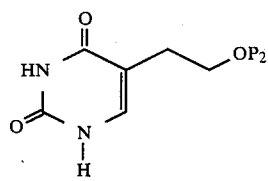

40 with a compound of formula 5 by methods analogous to those used for the preparation of 38 (wherein, for example, $X_6$ is hydrogen, methyl, or ethyl) followed by protection with the $P_3$ group by methods known in the art. The compound of formula 40 can be prepared from the compound of formula

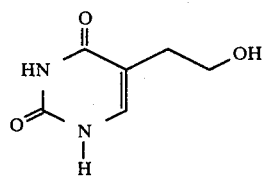

40a by methods known in the art.

The compound of formula

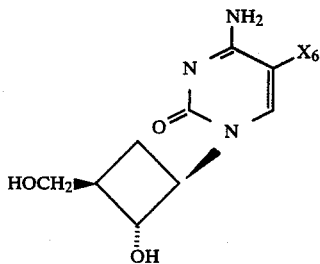

wherein X₆ is hydrogen, fluoro, methyl, ethyl, 2-chloroethyl, or 2-fluoroethyl can be prepared from the compound of formula

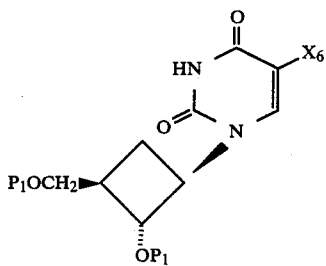

42

(wherein P₁ is a protecting group such as acyl, e.g., acetyl or benzoyl) by methods known in the art. See, for example, I. Wempner, et al. in "Synthetic Procedures in Nucleic Acid Chemistry", Vol. 1, W.W. Zorbach and R.S. Tipson, Eds., Interscience Publishers, N.Y., p. 299, 1968; T.S. Lin, et al., J. Med. Chem., 26, 1691 (1983); P. Herdewijn, et al., J. Med. Chem., 28, 550 (1985). Deprotection using methanolic ammonia or sodium methoxide in methanol yields a compound of formula 41. The compound of formula 42 can be prepared from the corresponding compound of formula 36 by methods known in the art.

Alternatively, the compound of formula 41 wherein X₆ is fluoro, hydrogen, methyl, ethyl, 2-chloroethyl, or 2-fluoroethyl, can be prepared by reaction of the corresponding compound of formula

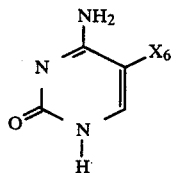

43 with a compound of formula 5 in the presence of a base such as potassium carbonate, sodium hydride, or potassium hydride in an aprotic solvent (e.g. dimethylformamide, dimethyl sulfoxide, or sulfolane), in the optional presence of 18-crown-6 or 15-crown-5, and subsequent removal of the protecting group P. Optionally, the amino (—NH₂) group in 43 can be protected (e.g., with an acyl group such as acetyl of benzoyl). Removal of this protecting group can be accomplished using sodium methoxide in methanol or methanolic ammonia.

Alternatively, the compound of formula 41 wherein X₆ is fluoro can be prepared from the corresponding compound wherein X₆ is hydrogen by fluorination with trifluoromethyl hypofluorite using methodology known in the art. Fluorination can also be performed on the compounds of formula 41 wherein X₆ is hydrogen and the hydroxyl and/or amino (—NH₂) groups are protected, for example, by an acyl such as acetyl or benzoyl. After fluorination, deprotection using methanolic ammonia or aqueous hydroxide affords the compound of formula 41 wherein X₆ is fluoro. See, for example, M. J. Robins, et al., J. Amer. Chem. Soc., 93, 5277 (1971) and Chem. Commun., 18 (1972); T. S. Lin, et al., J. Med. Chem., 26, 1691 (1983).

The compounds of formula 36 and 41 wherein X₆ is chloro, bromo, or iodo can be prepared from the corresponding compounds of formula 36 and 41 wherein X₆ is hydrogen by methods known in the art. See, for example, "Basic Principals in Nucleic Acid Chemistry", Vol. 1, P.O.P. Ts'O, Ed., Academic Press, N.Y., p. 146, 1974; P. K. Chang in "Nucleic Acid Chemistry" Part 3, L. B. Townsend and R. S. Tipson, Eds., John Wiley and Sons, N.Y., p. 46, 1986. For example, treatment of the compound of formula 36 wherein X₆ is hydrogen with iodine and nitric acid in aqueous dioxine affords the compound of formula 36 wherein X₆ is iodo.

The compounds of formula 36 and 41 wherein X₆ is trifluoromethyl can be prepared from the corresponding compounds of formula 36 and 41 wherein X₆ is iodo and the hydroxy groups are protected, for example, by an acyl (e.g., acetyl or benzoyl), by treatment with trifluoromethyl iodide and copper according to procedures known in the art. Subsequent deprotection using methanolic ammonia or sodium methoxide in methanol yields the corresponding compound of formulas 36 and 41 wherein X₆ is trifluoromethyl. See, for example, Y. Kabayashi, et al., J. Chem. Soc., Perkin 1, 2755 (1980); S. Lin, et al., J. Med. Chem. 26, 1691 (1983).

The compounds of formula 36 and 41 wherein X₆ is

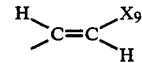

and X₉ is chloro, bromo, iodo, hydrogen or methyl can be prepared from the corresponding compounds of formula 36 and 41 wherein X₆ is iodo or HgCl via organopalladium intermediates. The compounds of formula 36 and 41 wherein X₆ is —HgCl can be prepared from the corresponding compounds of formula 36 and 41 wherein X₆ is hydrogen by methods known in the art. See, for example, references in E. DeClercq, et al., Pharm. Ther., 26, 1 (1984); M. E. Perlman, et al., J. Med. Chem., 28, 741 (1985); P. Herdewijn, et al., J. Med. Chem., 28, 550 (1985).

Compounds of the formula 1 wherein R₁ is

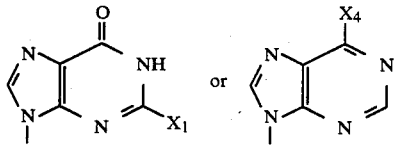

X₁ and X₄ are

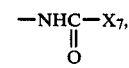

and R₂ and R₃ are hydrogen or

(or wherein $X_1$ and $X_4$ are amino) (—$NH_2$), and one or both of $R_2$ and $R_3$ are

can be prepared from the corresponding compounds of formula 1 wherein $X_1$ and $X_4$ are amino and $R_2$ and $R_3$ are hydrogen by methods known in the art.

All of the other compounds of formula 1 wherein one or both of $R_2$ and $R_3$ are

can be prepared by methods known in the art from the corresponding compounds of formula 1 wherein $R_2$ and $R_3$ are hydrogen.

For examples of acylation procedures, see "Synthetic Procedures in Nucleic Acid Chemistry", Vol. 1, W. W. Zorbach and R. S. Tipson, Eds., John Wiley and Sons, 1968; "Nucleic Acid Chemistry," Part 1, L. B. Townsend and R. S. Tipson, Eds., John Wiley and Sons, 1978; Y. Ishido, et al., *Nuclesides and Nucletides*, 5, 159 (1986); J. C. Martin, et al., *J. Pharm. Sci.*, 76, 180 (1987); A. Matsuda, et al., *Synthesis*, 385 (1986).

Compounds of the formula 1 wherein $R_1$ is

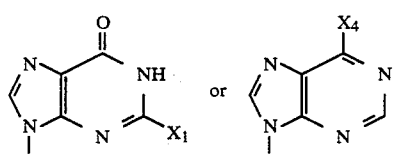

and $X_1$ and $X_4$ are —N=CHN($X_8$)$_2$ can be prepared from the corresponding compounds of formula 1 wherein $X_1$ and $X_4$ are amino by procedures known in the art. See, for example, A. Holy and J. Zemlicka, *Collect. Czech. Chem. Commun.*, 32, 3159 (1967); K. K. Ogilvie, et al., *Nucleosides and Nucletides*, 4, 507 (1985); M. H. Caruthers et al., *J. Amer. Chem. Soc.*, 108, 2040 (1986).

The compounds of formula 1 wherein $R_2$ and/or $R_3$ are —$PO_3H_2$ can be prepared from the corresponding compounds of formula 1 wherein $R_2$ and $R_3$ are hydrogen by procedures known in the art. See, for example, H. Schaller, et al., *J. Amer. Chem. Soc.*, 85, 3821 (1963); J. Beres, et al., *J. Med. Chem.*, 29, 494 (1986); R. Noyori, et al., *Tet. Lett.*, 28, 2259 (1987); W. Pfleiderer, et al., *Helv. Chim. Acta.*, 70, 1286 (1987); "Nucleic Acid Chemistry", Part 2, L. B. Townsend and R. S. Tipson, Eds., John Wiley and Sons, 1978.

The compounds of formula 1 wherein $R_1$ is

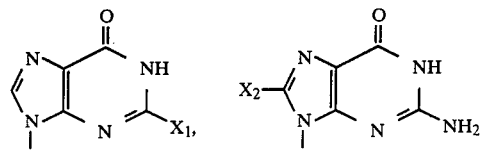

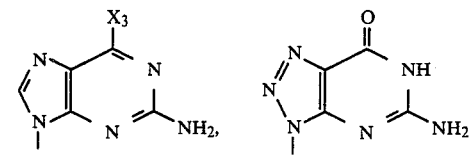

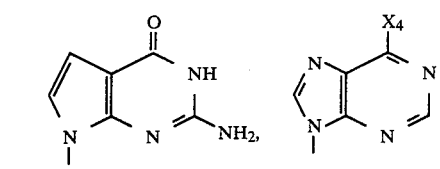

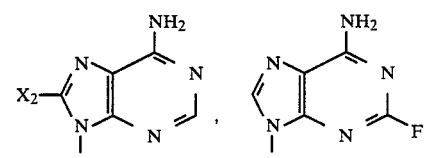

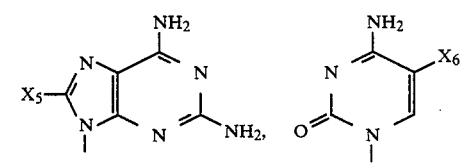

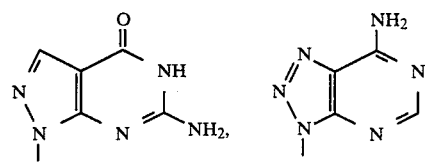

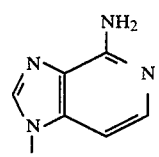

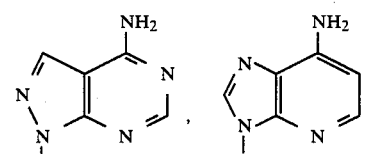

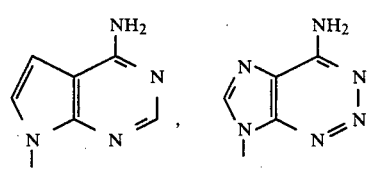

can form acid addition salts with inorganic or organic acids. Illustrative are the hydrohalide (e.g. hydrochloride and hydrobromide), alkylsulfonate, sulfate, phosphate and carboxylate salts.

The compounds of formula I wherein $R_1$ is

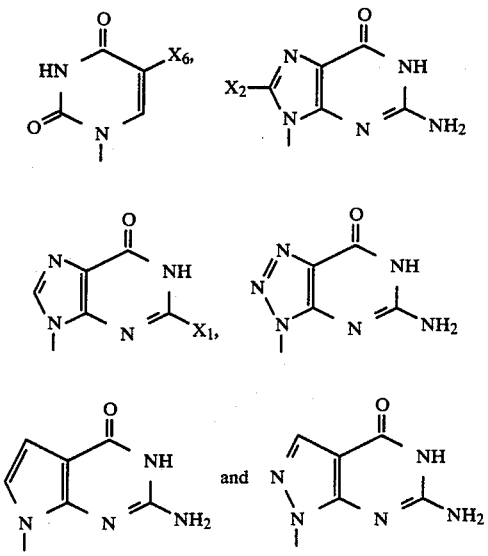

can form basic salts with inorganic and organic bases. Illustrative are alkali metal salts (e.g., sodium and potassium), alkaline earth metal salts (e.g., calcium and magnesium), ammonium and substituted ammonium salts.

The compounds of formula I wherein $R_2$ and/or $R_3$ are $-PO_3H_2$ can form basic salts with inorganic and organic bases. Illustrative are alkali metal salts (e.g., sodium and potassium), alkaline earth metal salts (e.g., calcium and magnesium), ammonium and substituted ammonium salts.

The stereochemistry shown for the compounds of this invention is relative, not absolute. It is drawn to show that in the compounds of this invention, the base ($R_1$) is cis with respect to the $-CH_2-OR_2$ substituent and trans with respect to the $OR_3$ substituent.

The following examples are specific embodiments of this invention.

EXAMPLE 1

(1α,2β,3α)-9-[2-Hydroxy-3-(hydroxymethyl)-cyclobutyl]guanine (A) [[(3-Chlorocyclobutyl)methoxy]methyl]benzene A mixture of 3-chlorocyclobutanemethanol (17.3 g, 0.143 mole) and benzylbromide (26.96 g, 0.158 mole) in dry dimethylformamide (123 ml) was stirred at room temperature under an argon atmosphere and a 60% suspension of sodium hydride (6.31 g 0.158 g mole) was added. The reaction was stirred at ambient temperature for 22.5 hours. The reaction mixture was poured into 600 ml of water and the aqueous mixture extracted with ethyl acetate (4×500 ml). The ethyl acetate extracts were combined and dried over anhydrous sodium sulfate and the ethyl acetate evaporated in vacuo yielding the crude product as a yellow oil. The material was purified on a 2-liter Merck silica gel column eluting with 3 liters of hexane, followed by 5% ethyl acetate/hexane. The fractions containing the desired product were combined and the volatiles evaporated in vacuo yielding 28.6 g of the title compound as a pale yellow oil.

(B) [(2-Cyclobuten-1-ylmethoxy)methyl]benzene

[[(3-Chlorocyclobutyl)methoxy]methyl]benzene 82 g, 0.39 mole) in 390 ml of dry dimethylsulfoxide was slowly added to a solution of potassium t-butoxide (132 g, 1.17 mole) in 390 ml of dry dimethylsulfoxide in a water-bath at 18° C. under a dry argon atmosphere. After stirring for 1 hour at room temperature, the reaction mixture was poured into 1600 ml of water and extracted with ether (3×1000 ml). The combined ether extracts were back-extracted with water (4×2000 ml), the extracts were then dried over sodium sulfate, and the volatiles were removed in vacuo. The crude product was divided into two equal portions and each portion was purified on separate 3.5 liter Merck silica columns, eluting with 3% ethyl acetate-hexane. Appropriate fractions were combined and the solvents removed in vacuo yielding 60.0 g of the title compound as a colorless liquid.

(C) (1α,2α,4α)-2-[(Phenylmethoxy)methyl]-5-oxabicyclo[2.1.0]pentane

A solution of 80% m-chloroperoxybenzoic acid (19.0 g, 0.088 mol) in 600 ml of dichloromethane was cooled to 0° C. and a solution of [(2-cyclobuten-1-ylmethoxy)-methyl]benzene (14.0 g, 0.080 mol) in 50 ml of dichloromethane was added and the resulting mixture was stirred overnight at 5° C. under an argon atomsphere. The precipitated m-chlorobenzoic acid was removed by filtration, and the dichloromethane solution was washed with 5% sodium thiosulfate (1×500 ml), saturated sodium bicarbonate (3×500 ml), and water (2×500 ml). The dichloromethane solution was then dried over anhydrous sodium sulfate. The solution was filtered and the dichloromethane was evaporated in vacuo yielding 11.6 g of 1:1 mixture of cis and trans product.

A quantity of the cis an trans isomers (1:1) were separated by preparative HPLC using a "Water's Prep 500" with a 500 ml silica gel column eluting with 2.5% ethyl acetate/hexane loading 2 g of mixture at 100 ml/minute and then eluting the column at a flow rate of 200 ml/minute (total 10 g of mixture used). Peak shaving technique was used to enrich one isomer over the other, with the mixture being recycled through the column 3 times. A total of 2.1 g of trans epoxide and 2.48 g of cis epoxide were separated.

ALTERNATIVE SEPARATION OF CIS AND TRANS ISOMERS

A crude mixture of cis and trans epoxide (1:1, 58 g) was isolated from two separate m-chloroperoxybenzoic acid oxidations of two 27.05 g batches of [(2-cyclobuten-1-ylmethoxy)methyl]benzene following the general procedure described above. Two equal 29 g portions were purified on two separate 3.5 liter silica gel columns eluting with 5% ethyl acetate/pentane. The fractions containing essentially pure (1α,2α,4α)-2-[(phenylmethoxy)methyl]-5-oxabicyclo[2.1.0]pentane were combined and the solvents removed in vacuo yielding 4.02 g of desired compound. Those fractions containing a greater than 1:1 ratio of trans epoxide were combined and the solvents removed in vacuo yielding 20.5 g of a mixture enriched in trans epoxide.

The trans-enriched mixture was further purified by preparative HPLC using a "Waters Prep 500" equipped with two tandem 500 ml silica gel columns eluting with 5% ethyl acetate/pentane loading 4 g of the mixture at a time (at a flow rate of 250 ml/minute). A total of 20.5 g of material was loaded in this fashion. Peak shaving technique was used to enrich one isomer over the other, with the mixture being recycled back through the column once. Eventually, 6.91 g of essentially pure (1α,2α,4α)-2-[(phenylmethoxy)-methyl]-5-oxabicyclo[2.1.0]pentane was isolated in this fashion. Total recovery was 10.93 g.

ALTERNATIVE EPOXIDATION REACTION

To a mixture of benzonitrile (0.80 ml, 7.8 mmol) and potassium bicarbonate (170 mg, 1.7 mmol) in 12 ml of methanol was added [(2-cyclobuten-1-ylmethoxy)methyl]benzene (523 mg, 3.0 mmol) in 12 ml of chloroform followed by the addition of 1 ml of 30% hydrogen peroxide. The mixture was rapidly stirred at room temperature under an argon atmosphere for 92 hours. The reaction was poured into 75 ml of 5% sodium thiosulfate and was extracted with 200 ml of ether. The ether extract was washed with 200 ml of water, 200 ml of saturated sodium bicarbonate and 200 ml of saturated sodium chloride solution. The ether extract was dried over anhydrous sodium sulfate, filtered and the ether removed in vacuo yielding 1.1 grams of crude mixture. The crude material was purified on a 100 ml Merck silica column eluting with 500 ml of hexanes followed by eluting with 1000 ml of 2½% ethyl acetate/hexanes. All fractions containing cis and trans-epoxide were combined. The volatiles were removed in vacuo yielding 478 mg of a 1:2.5 mixture of cis and trans isomers, respectively.

(D)
(1α,2β,4β)-2[2-Amino-6-(phenylmethoxy)-9H-purine-9-yl]-4-[(phenylmethoxy)methyl]cyclobutanol Freshly dried (65° C. @ 0.1 mm Hg overnight) 2-amino-6-benzyloxypurine (1.21 g, 5.0 mmol) and (1α,2α,4α)-2-[(phenylmethoxy)methyl]-5-oxabicyclo-[2.1.0]-pentane (571 mg, 3.0 mmol) were dissolved in 13 ml of dry dimethylformamide under an argon atmosphere. 60% Sodium hydride (60 mg, 1.5 mmol) was added to the reaction mixture at room temperature and the reaction was then heated at 110° C. for 3 days. The reaction was cooled to room temperature and the dimethylformamide was evaporated under vacuum at 40° C. yielding the crude product as a brown solid. The residue was partially dissolved in 8 ml of dichloromethane and purified on a 500 ml Whatman LPS1 silica column eluting with 1500 ml of dichloromethane followed by 300 ml of 2% methanol/dichloromethane collecting 20 ml fractions. The fractions containing pure product were combined and the volatiles removed in vacuo yielding the title compound as a colorless solid, 336 mg.

ALTERNATIVE REACTION

To a stirring suspension of (1α,2α,4α)-2-[(phenylmethoxy)methyl]-5-oxabicyclo[2.1.0]pentane (57.1 mg, 0.30 mmol), 2-amino-6-benzyloxypurine (121.0 mg, 0.50 mmol, dried for 24 hours at 80° C., 1 mm Hg, over P$_2$O$_5$), and 18-crown-6 ether (61.0 mg, 0.23 mmol) in sulfolane (1.3 ml, dried over 3° A. molecular sieves) at room temperature under argon was added sodium hydride (7.0 mg, 0.175 mmol, 60% oil dispension). After the mixture was heated to 110° C., the solution became homogeneous. After 21 hours at 110° C., the reaction was cooled to room temperature and was quenched with acetic acid (0.025 ml).

Most of the solvent was removed by distillation (0.3 mm Hg) leaving an orange oily residue. This residue was purified by silica gel chromatography (Merck 230–400 mesh), eluting with CH$_2$Cl$_2$, 1%, 2%, and then 3% MeOH:CH$_2$Cl$_2$ to give the pure coupled product (54.8 mg).

(E)
(1α,2β,3α)-9-[2-Hydroxy-3-(hydroxymethyl)cyclobutyl]guanine (1α,2β,4β)-2-[2-Amino-6-(phenylmethoxy)-9H-purin-9-yl]-4-[(phenylmethoxy)methyl]cyclobutanol (336 mg, 0.78 mmol) in 3 ml of dry, distilled tetrahydrofuran was added to 30 ml of liquid ammonia at −78° C. under an argon atmosphere. With stirring, finely cut sodium (165 mg, 7.2 mmol) was added and when the mixture became dark blue in color the cooling bath was removed and the mixture was allowed to stir for 10 minutes. The reaction was quenched by adding small portions of ammonium chloride until the reaction became colorless. The volatiles were then removed by allowing a slow stream of nitrogen to pass through the reaction mixture yielding the crude product as a colorless solid. The crude solid was dissolved in 20 ml of water and the pH was adjusted from pH 12.6 to pH 7.0 by adding 1N hydrochloric acid solution. When the pH reached 10 the product began to precipitate from solution. The precipitated product was collected by centrifugation and was washed twice with col water (2×4 ml). The resulting colorless solid was dried in vacuo overnight at room temperature yielding 134 mg of the title product, melting point 246° C. (dec.)

| Anal. | Calc'd. for C$_{10}$H$_{13}$N$_5$O$_3$.1.25H$_2$O: |
|---|---|
| | C, 43.74; H, 5.72; N, 25.51 |
| found: | C, 43.43; H, 5.53; N, 25.83. |

EXAMPLE 2
(1α,2β,3α)-3-(6-Amino-9H-purin-9-yl)-2-hydroxycyclobutanemethanol

(A)
(1α,2β,4β)-2-(6-Amino-9H-purin-9-yl)-4-[(phenylmethoxy)methyl]cyclobutanol A mixture of dried adenine (557 mg, 4.125 mmol) and (1α,2α,4α)-2-[(phenylmethoxy)methyl]-5-oxabicyclo[2.1.0]pentane (523 mg, 2.75 mmol; see example 1C) was partially dissolved in 5.5 ml of dry dimethylformamide under an argon atmosphere. To this mixture was added potassium carbonate (95 mg, 0.69 mmol) followed by 18-crown-6 ether (330 mg, 1.25 mmol) and then the mixture was heated at 110° C. for 50 hours. The reaction was cooled to room temperature, and the volatiles were removed under vacuum at 40° C. yielding the crude product as a brown solid. The residue was partially dissolved in 10 ml of dichloromethane and purified on a 250 ml Whatman LPS1 silical gel column, eluting with 750 ml of dichloromethane followed by 2000 ml of 2½% methanol/dichloromethane. The fractions containing the pure desired product were combined and the volatiles removed in vacuo yielding the title compound as a colorless solid, 212 mg.

(B)
(1α,2β,3α)-3-(6-Amino-9H-purin-9yl)-2-hydroxycyclobutanemethanol (1α,2β,4β)-2-(6-Amino-9H-purin-yl)-4-[(phenylmethoxy)methyl]cyclobutanol (200 mg, 0.615 mmol) was dissolved in 40 ml of absolute ethanol and 20 ml of cyclohexene. 20% Palladium hydroxide (140 mg) was added and the mixture was heated at reflux for 24 hours. At this point, an additional 70 mg of 20% palladium hydroxide catalyst was added, and after another 8 and 10 hours two 70 mg portions of catalyst were again added. After refluxing for a total of 66 hours, the reaction was filtered through a "milipore" filter to remove the catalyst and the catalyst was washed with approximately 10 ml of ethanol. The volatiles were removed in vacuo yielding the crude product as a colorless solid. The material was dissolved in 5 ml of water and purified on a 50 ml HP-20 column eluting with 600 ml of a 50% acetonitrile-water/water gradient. The fractions containing pure product were combined, the acetonitrile removed in vacuo, and the water lyophilized to yield 59 mg of product as a colorless solid, melting point 240° (dec.).

EXAMPLE 3
(1α,2β,3α)-2-Amino-1,9-dihydro-9-[2-hydroxy-3-(hydroxymethyl)cyclobutyl]-8-methyl-6H-purin-6-one Nitrogen was bubbled through a solution of (1α,2β,3α)-9-[2-hydroxy-3-(hydroxymethyl)cyclobutyl]guanine (74 mg; 0.3 mmol) and $FeSO_4 \cdot 7H_2O$ (278 mg; 1 mmol) in 16 ml of 1M $H_2SO_4$ to remove traces of oxygen. After 30 minutes the reaction was blanketed with argon and tertiary butyl hydroperoxide (500 mg, 70% solution in water; 4 mmol) in 3 ml of water was added dropwise over 30 minutes. After stirring for 2 hours, the reaction mixture was neutralized with 1N NaOH and the resulting dark brown suspension was centrifuged to remove the viscous brown sludge. The clear colorless supernate was loaded onto an HP-20 column (2.5×15 cm) which was eluted with 1 liter of water followed by a linear gradient from water to 25% acetonitrile-water. The pure desired fractions were concentrated and lyophilized to afford 37 mg of the title product as a white solid having m.p. 228°–232° C. (dec.).

EXAMPLE 4
(1α,2β,3α)-2-Amino-8-bromo-1,9-dihydro-9-[2-hydroxy-3-(hydroxymethyl)cyclobutyl]-6H-purin-6-one (1α,2β,3α)-9-[2-Hydroxy-3-(hydroxymethyl)cyclobutyl]guanine (225 mg; 0.9 mmol) was suspended in water (35 ml) at room temperature. Bromine water (which was prepared by stirring 2 ml of bromine in 75 ml of water and decanting off the supernatant after 10 minutes) (7 ml) was added dropwise over 5 minutes. After this addition, the suspension became a solution for five minutes, and then a precipitate reappeared. TLC (Silica gel, 6:3:1, chloroform:methanol:conc. ammonia) of an aliquot of the suspension dissolved in dimethylformamide showed only partial reaction. An additional 2 ml of bromine water was added and the TLC showed that a trace of starting material remained. Then 0.5 ml of bromine water was added. After a total reaction time of approximately 1 hour, the reaction mixture was cooled to 0° C. The solid was filtered, washed with cold water, and dried to afford 292 mg, of crude title product. A 120 mg portion was recrystallized from hot water to afford 112 mg, of the title product as an off white solid having m.p. >240° C.

EXAMPLE 5
(1α,2β,3α)-2,8-Diamino-1,9-dihydro-9-[2-hydroxy-3-(hydroxymethyl))cyclobutyl]-6H-purine-6-one.

(1α,2β,3α)-2-Amino-8-bromo-1,9-dihydro-9-[2-hydroxy-3-(hydroxymethyl))cyclobutyl]-6H-purine-6-one (155 mg; 0.47 mmol) was refluxed in 7 ml of water and 0.36 ml of hydrazine-hydrate for 168 hours (7 days). After each 24 hour period, 0.2 ml of hydrazine-hydrate and 0.5 ml of water were added to the refluxing suspension. The solvents were removed in vacuo and the white solid residue was triturated with water to remove inorganics. The residue was loaded onto an HP-20 column (2.5×45 cm) which was eluted with a continuous gradient from water to water-dimethylformamide, 1:1. The pure product containing fractions were concentrated to a white powder. This powder was suspended in water and filtered to remove residual dimethylformamide. Drying in vacuo for 18 hours over $CaSO_4$ afforded 50 mg of the title product as a white powder having m.p. 225° C. (dec.).

EXAMPLE 6
(1α,2β,3α)-1-[2-Hydroxy-3-(hydroxymethyl)cyclobutyl]-5-methyl-2,4(1H,3H)-pyrimidinedione A.
(1α,2β,3α)-1-[2-Hydroxy-3-((phenylmethoxy)methyl)cyclobutyl]-5-methyl-2,4(1H,3H)-pyrimidinedione.

A mixture of dried thymine (380 mg, 3.0 mmol) and 1α,2α,4α-[(phenylmethoxy)methyl]-5-oxabicyclo[2.1.0]pentane (380 mg, 2.0 mmol) were dissolved in 4 ml of dimethylformamide under an argon atmosphere. To this mixture was added potassium carbonate (35 mg, 0.25 mmol) followed by 18-crown-6 (120 mg, 0.45 mmol) and then the mixture was heated at 110° C. for 68 hours. The reaction progress was monitored by TLC. The reaction was cooled to room temperature, a few drops of acetic acid was added and the mixture stirred for 20 minutes. The valatiles were removed at 40° on the "Kugelrohr" apparatus yielding the crude product as a brown solid. The residue was partially dissolved in 8 ml of methylene chloride and purified on a 400 ml Whatman LPS-1 silica column eluting with 800 ml of methylene chloride followed by 1200 ml of 2% methanol-methylene chloride collecting 12 ml fractions. The fractions containing the pure desired product were combined and the volatiles removed in vacuo yielding the title product as a colorless solid, 70 mg.

(B)
(1α,2β,3α)-1-[2-Hydroxy-3-(hydroxymethyl)cyclobutyl]-5-methyl-2,4(1H,3H)-pyrimidinedione.

(1α,2β,3α)-1-[2-Hydroxy-3-(phenylmethoxy)methyl)-cyclobutyl]-5-methyl-2,4(1H,3H)-pyrimidinedione (70 mg, 0.22 mmol) was dissolved in 6 ml of 95% ethanol and 2 ml of cyclohexene. 20% Palladium hydroxide (70 mg) was added and the mixture was stirred 26 hours at room temperature. TLC showed no starting material remaining. The catalyst was removed by filtering through a "Millipore" filter and washing the catalyst with 10 ml of EtOH. The volatiles were removed in vacuo yielding the crude product as a colorless solid. The material was dissolved in 4 ml of water containing a few drops of acetonitrile and purified on a 20 ml HP-20 column, eluting the column with 200 ml of a 50% acetonitrile-water/water gradient, collecting 6 ml fractions. The fractions containing pure product were combined, the acetonitrile was removed in vacuo, and the water lyophilized to yield 42 mg of the title product as a colorless solid having m.p. 186° C. (dec).

EXAMPLE 7

(1α,2β,3α)-4-Amino-1-[2-hydroxy-3-(hydroxymethyl)-cyclobutyl]-2(1H)-pyrimidinone.

(A)

(1α,2β,3α)-4-Amino-1-[2-hydroxy-3-(phenylmethoxy)-methyl)cyclobutyl]-2(1H)-pyrimidinone.

A mixture of (1α,2α,4α)-2-[(phenylmethoxy)methyl]-5-oxabicyclo[2.1.0]pentane (380 mg; 2 mmol), cytosine (456 mg; 4.1 mmol), 18-crown-6 (400 mg, 1.5 mmol), and K$_2$CO$_3$ (140 mg, 1 mmol) was stirred in sulfolane (8 ml) at 120° C. for 24 hours. The solvent was removed by Kugelrohr distillation under high vacuum at 85° C. The residue was loaded onto a 2.5×40 cm silica gel column. The column was eluted with a stepwise gradient from methylene chloride to 16% methanol-methylene chloride. The pure practions containing desired compound were concentrated to afford 280 mg of the title compound contaminated with 18-crown-6. Trituration with diethyl ether and drying afforded 240 mg* of the title compound (*This material was 89% pure by 270 MHz NMR. The impurity, 18-crown-6 was 11% and accounted for 29 mg. Corrected yield: 211 mg).

(B)

(1α,2β,3α)-4-Amino-[2-hydroxy-3-(hydroxymethyl)cyclobutyl]-2(1H)-pyrimidinone.

A mixture of (1α,2β,3α)-4-amino-1-[2-hydroxy-3-(phenylmethoxy)methyl)cyclobutyl]-2(1H)-pyrimidinone (175 mg; 0.58 mmol), 20% Pd(OH)$_2$ on carbon (175 mg) and cyclohexene (4.3 ml) was heated at reflux in 20 ml of 95% ethanol for 6 hours. The mixture was filtered through celite and the filter cake was washed well with 95% ethanol. The filtrate was concentrated to dryness and co-evaporated with water (2×20 ml) to drive off residual ethanol. The residue was loaded onto a HP-20 column (2.5×20 cm) and was eluted with a continuous gradient from water to 30% acetonitrile-water. Pure fractions were concentrated and lyophilized to afford 87 mg of the title product as a fluffy white solid having m.p. 205°–210° C. (dec).

EXAMPLE 8

(1α,2β,3α)-1-[2-Hydroxy-3-(hydroxymethyl)cyclobutyl]-2,4(1H,3H)-pyrimidinedione (A)

(1α,2β,3α)-1-[2-Hydroxy-3-(phenylmethoxy)methyl)-cyclobutyl]-2,4(1H,3H)-pyrimidinedione A mixture of (1α,2α,4α)-2-[phenylmethoxy)methyl]-5-oxabicyclo[2.1.0]pentane (0.552 g, 2.9 mmol), uracil (1.3 g, 11.6 mmol), NaH (65 mg of a 60% suspension, 1.62 mmol), and 18-crown-6 (0.61 g, 2.3 mmol) in sulfolane (13 ml) was heated at 115° C. for 110 hours. The reaction mixture was quenched with acetic acid (0.1 ml) and the solvent was removed by Kugelrohr distillation (80° C., 0.25 mm Hg). The orange oily solid residue was preadsorbed on silica gel (Baker reagent, 60–230 mesh) and purified by flash chromatography (silica gel, 230-400 mesh, 5 cm×33 cm), eluting with methylene chloride and then a stepwise gradient of methanol-methylene chloride (1–5%). This gave the title compound (0.37 g) as a colorless powder.

(B)

(1α,2β,3α)-1-[2-Hydroxy-3-(hydroxymethyl)cyclobutyl]-2,4(1H,3H)-pyrimidinedione

A mixture of (1α,2β,3α)-1-[2-hydroxy-3-(phenylmethoxy)methyl)cyclobutyl]-2,4(1H,3H)-pyrimidinedione (0.37 g, 1.22 mmol), cyclohexene (7.5 ml), and Pd(OH)$_2$ (0.38 g, 20% on carbon) in aqueous ethanol (95%, 30 ml) was refluxed for 3 hours. After cooling, the mixture was filtered through Celite and washed well with ethanol. The residue was purified on HP20 (3×26 cm), eluting first with water and then a gradient of water/acetonitrile-water (1:1). The fractions containing pure compound were concentrated and the residue lyophilized to give the title compound (0.168 g) as a colorless solid. Proton NMR (400 MHz, DMSO-d$_6$) ppm: 11.19 (broad singlet, 1H), 7.65 (doublet, J=8 Hz, 1H), 5.61 (doublet, J=8 Hz, 1H), 5.44 (doublet, J=6 Hz, 1H), 4.52 (triplet, J=5 Hz, 1H), 4.39 (multiplet, 1H), 3.97 (multiplet, 1H), 3.50 (multiplet, 2H), 2.05 (doublet of doublets, J=9, 20 Hz, 1H), 1.91 (multiplet, 1H), 1.35 (doublet of doublets, J=10, 20 Hz, 1H).

EXAMPLE 9

(1α,2β,3α)-1-[2-Hydroxy-3-(hydroxymethyl)cyclobutyl]-5-iodo-2,4(1H,3H)-pyrimidinedione A mixture of (1α,2β,3α)-1-[2-hydroxy-3-(hydroxymethyl)cyclobutyl]-2,4(1H,3H)-pyrimidinedione (58.1 mg, 0.275 mmol), iodine (140 mg, 0.55 mmol) and HNO$_3$ (aqueous, 0.36 ml of 0.8N) in dioxane (6 ml, passed through basic alumina) was refluxed for 10 hours. After cooling to room temperature, the excess iodine was reduced with a minimum of solid sodium thiosulfate. The resulting mixture was purified by HP-20 (3 cm×25 cm column), eluting with water and then a gradient of water/acetonitrile-water (1:1). The fractions containing pure compound were concentrated to give a slightly yellow solid (93 mg). This solid was recrystallized from hot water to give the title product (66 mg) as a colorless solid having m.p. 99°–101° C.

What is claimed is:

1. A compound having the formula

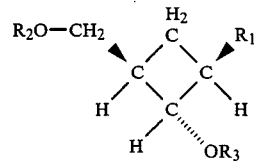

or a pharmaceutically acceptable salt thereof, wherein R$_1$ is

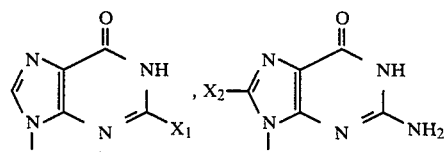

-continued

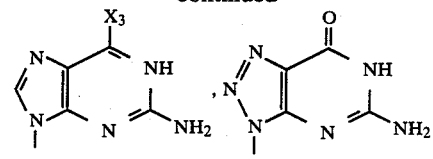

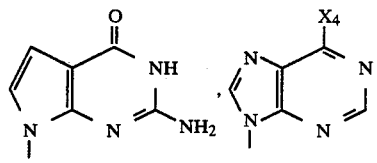

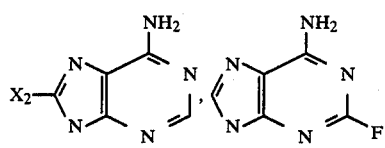

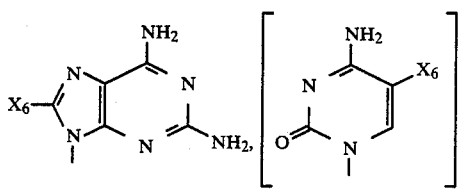

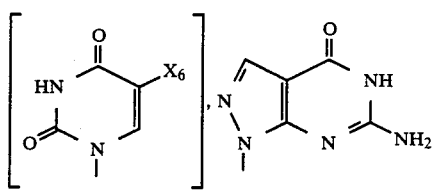

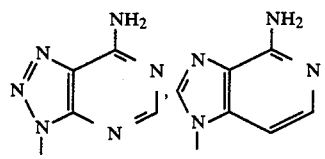

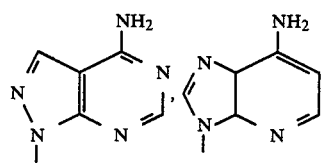

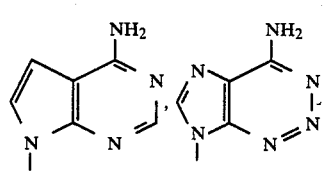

wherein
$X_1$ is hydrogen, amino,

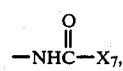

and —N=CHN$(X_8)_2$
$X_2$ is methyl, fluoro, chloro, bromo, iodo, hydroxy, or amino,
$X_3$ is hydrogen, chloro, or O—$X_8$,
$X_4$ is amino,

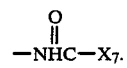

or —N=CHN$(X_8)_2$,
$X_5$ is hydrogen, methyl, fluoro, chloro, bromo, iodo, hydroxy, or amino,
$X_6$ is fluoro, chloro, bromo, iodo, hydrogen, methyl, trifluoromethyl, ethyl, 2-fluoroethyl, 2-chloroethyl, or

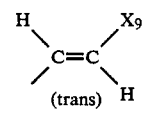

$X_7$ is hydrogen, alkyl, substituted alkyl, or aryl,
$X_8$ is alkyl,
$X_9$ is chloro, bromo, iodo, hydrogen, or methyl,
$R_2$ and $R_3$ are independently hydrogen, —PO$_3$H$_2$, or

2. A compound in accordance with claim 1 wherein $R_1$ is

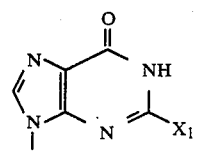

or

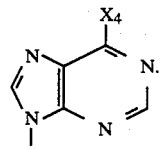

3. A compound in accordance with claim 2 wherein $R_1$ is

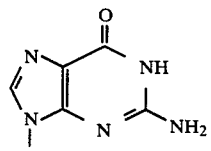

4. A compound in accordance with claim 2 wherein $R_1$ is

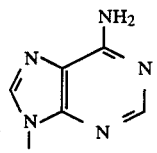

5. A compound in accordance with claim 1 wherein $R_2$ and $R_3$ are independently hydrogen or

6. A compound in accordance with claim 1 wherein $R_2$ and $R_3$ are independently hydrogen or —$PO_3H_2$.
7. A compound in accordance with claim 6 wherein $R_2$ and $R_3$ are hydrogen.
8. A compound in accordance with claim 3 wherein $R_2$ and $R_3$ are independently hydrogen or

9. A compound in accordance with claim 3 wherein $R_2$ and $R_3$ are independently hydrogen or —$PO_3H_2$.
10. A compound in accordance with claim 4 wherein $R_2$ and $R_3$ are independently hydrogen or

11. A compound in accordance with claim 4 wherein $R_2$ and $R_3$ are independently hydrogen or —$PO_3H_2$.
12. A compound in accordance with claim 1 wherein $R_1$ is

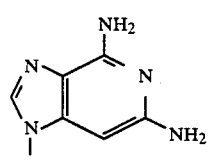

13. A compound in accordance with claim 1 wherein $R_1$ is

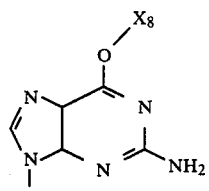

14. A compound in accordance with claim 1 wherein $R_1$ is

15. A compound in accordance with claim 1 wherein $R_1$ is

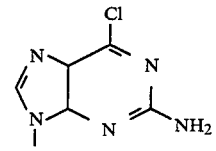

16. A compound in accordance with claim 1 wherein $R_1$ is

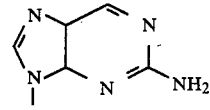

17. A compound in accordance with claim 1 wherein $R_1$ is

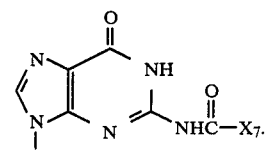

18. A compound in accordance with claim 1 wherein $R_1$ is

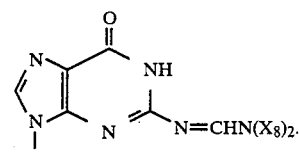

19. A compound in accordance with claim 1 wherein $R_1$ is

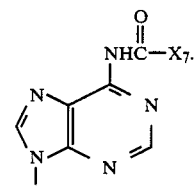

20. The compound in accordance with claim 1, (1α,2β,3α)-9-[2-hydroxy-3-(hydroxymethyl)cyclobutyl]guanine.

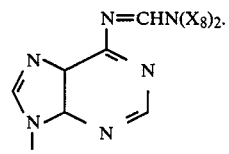

21. The compound in accordance with claim 1, (1α,2β,3α)-3-(6-amino-9H-purin-9-yl)-2-hydroxycyclobutanemethanol.

22. The compound in accordance with claim 1, (1α,2β,3α)-2-amino-1,9-dihydro-9-[2-hydroxy-3-(hydroxymethyl)cyclobutyl]-8-methyl-6H-purin-6-one.

23. The compound in accordance with claim 1, (1α,2β,3α)-2-amino-8-bromo-1,9-dihydro-9-[2-hydroxy-3-(hydroxymethyl)cyclobutyl]-6H-purin-6-one.

24. The compound in accordance with claim 1, (1α,2β,3α)-2,8-diamino-1,9-dihydro-9-[2-hydroxy-3-(hydroxymethyl))cyclobutyl]-6H-purine-6-one.

25. A method of treating a viral infection in a mammalian or avian host in need thereof, which comprises administering to said host an effective amount of a compound as defined in claim 1.

* * * * *